United States Patent [19]

Rye

[11] Patent Number: 5,166,536
[45] Date of Patent: Nov. 24, 1992

[54] METHOD AND APPARATUS FOR DETECTING EDGE CRACKS

[76] Inventor: Timothy W. Rye, 1109 Tom La., Marietta, Ga. 30066

[21] Appl. No.: 654,204

[22] Filed: Feb. 11, 1991

[51] Int. Cl.$^5$ ............................................ G01N 21/89
[52] U.S. Cl. ...................................... 250/572; 250/571
[58] Field of Search ................ 250/572, 571, 563, 548

[56] References Cited

U.S. PATENT DOCUMENTS

| | | | |
|---|---|---|---|
| 4,786,817 | 11/1988 | Boissevain et al. | 250/571 |
| 4,938,601 | 7/1990 | Weber | 250/572 |
| 5,024,156 | 6/1991 | Hank et al. | 250/548 |

OTHER PUBLICATIONS

Ulma Brochure #1.
Ulma Brochure #2.
Ulma Operating Instructions.
Afora Autospec Brochure.
Rayex Brochure.
Intec Brochure #1.
Roibox Brochure.
Intec Brochure #2.
"Laser vs. Camera Inspection in the Paper Industry", Joseph D. Paumi, 1988.

*Primary Examiner*—Constantine Hannaher
*Assistant Examiner*—Richard Hanig
*Attorney, Agent, or Firm*—Louis T. Isaf

[57] ABSTRACT

A method for detecting both separated and non-separated edge cracks on a travelling product, such as a continuous paper web, and the like, and an apparatus for performing the invented method. The method includes directing air onto a travelling product with sufficient force to separate non-separated edge cracks and utilizing an optical signal device to detect edge cracks in the travelling product. A preferred embodiment of the method includes directing two streams of air toward opposite surfaces of the travelling product to effectively separate the non-separated edge cracks and orienting the optical device so that the direction of emitted optical signals forms an angle other than a right angle with the direction in which the product is travelling. The air used to separate the non-separated cracks is also directed across the optical signal device to prevent the build-up of foreign particles, thus improving the integrity of the method. The method also involves automatically tracking the edge of the travelling product and moving the optical sensing device along with the edge of the travelling product so that the optical signal device is continuously positioned at a predetermined distance from the edge of the product. An apparatus for performing the invented method includes an air-purged housing which forms an air delivery opening, and an optical sensor located within the air-purged housing which directs optical signals through the air delivery opening.

35 Claims, 6 Drawing Sheets

METHOD AND APPARATUS FOR DETECTING EDGE CRACKS

BACKGROUND OF THE INVENTION

The present invention relates generally to the field of monitoring travelling products, and more specifically, to the field of detecting edge cracks on continuous paper webs.

It is well known that during the manufacture of continuous, travelling products, such as paper webs, cracks in the edges of the products often appear. Besides reducing the level of quality of the finished product, unattended cracks often lead to breaks in the product during high tension stages of the process. The full extent of the harmful consequences of a break in a high speed process is also well known in the industry. The large amount of time it takes to repeatedly stop the process, clean-up the results of the break, and re-start the process translates into a very large amount of cost to a manufacturer.

The early detection of an edge crack in a travelling product is desirable because it can enable a manufacturer to appropriately react to such a crack. One type of reaction involves easing the tension normally applied to the product during high tension stages of the process while the cracked portion travels through that stage. In some cases, a simple slowing of the process may adequately relieve the tension. Another type of reaction involves selectively trimming the edge of the product around the crack. A smooth, gradual cut in the product is known to be much stronger than an edge crack.

When faced with the costs related to frequent breaks and the problem of reliably detecting edge cracks, some manufactures routinely trim away large continuous portions along the edge of the product in an effort to eliminate all of the area susceptible to cracks before the product reaches the high tension stages of the process. This procedure is obviously very wasteful and is also unreliable, given known limitations of common trimmers.

There have been some attempts to design comprehensive fault detection systems to detect most types of faults located across the entire width of the product. Most of these systems are extremely expensive, involve a multitude of elements, and are difficult to operate and maintain. Although many of these systems claim to be able to detect edge cracks, all have limitations which characterize the existing problems in the art of detecting edge cracks.

There are at least two major types of edge cracks which are frequently encountered: separated & non-separated. Separated edge cracks are those edge cracks which are readily seen from above as gaps. Typically, at least one portion of the product adjacent to the crack is folded back over itself to reveal a large, sharply angled hole. A few of the current fault detection systems are relatively effective in detecting these types of separated edge cracks where the crack is visible from directly above the crack. The second major type of edge crack, the non-separated edge crack, is not readily seen from above as a gap. With this type of crack, both portions of the product adjacent to the crack are so close to each other that there is no gap readily visible from directly above the crack. There is currently a great need in the industry for a system which will effectively detect non-separated edge cracks.

Of the types of systems which are relatively effective at detecting separated edge cracks only, a first type of system utilizes one or more cameras positioned directly above the travelling product. The cameras continually take segmented pictures of the product as it travels directly below. The pictures are broken down into very small segments and analyzed for various types of faults. This analysis process normally requires a high-powered, and consequently high-priced, computing device to continuously process the very large amount of data. Because some travelling products travel very quickly, the camera systems are required to scan very rapidly to be able to detect the smaller faults.

Assuming the scan rate can be adjusted to accommodate both the speed of the travelling product and the size of a separated edge crack, these camera systems may be used to detect separated edge cracks. By comparing successive positions of the edges between scans, a crack is assumed to have been found when the values differ greatly. That is, when the edge wanders in very rapidly, a crack signal is generated. This method, when considered in light of the complicated construction, the high cost, and the relative slowness, is not very efficient at detecting separated edge cracks. Furthermore, because non-separated edge cracks often appear from above as continuous sections of product, this type of system is virtually ineffective at detecting the common non-separated edge cracks.

A second type of system utilizes one or more rapidly scanning lasers. These systems deploy rapidly moving parts, such as mirrors, which direct one or more laser beams directly down onto the product and transversely across the width of the travelling product. Besides having problems associated with these continuously moving parts, the problem of missing a crack between scans is also readily apparent. During the time in which the laser is scanning other parts of the product, a very thin crack in a rapidly travelling product may pass the point at which the laser scans. Furthermore, problems similar to those associated with the camera systems often exist with these laser systems too.

A third type of system involves a series of phototransistors positioned above the product in a line across the width of the product. Light is supplied to the underside of the product by a continuous light source positioned below the series of phototransistors. The intensity of the light transmitted through the product is monitored and used to detect faults. Because the edges of many travelling products wander, screens are routinely placed over a predetermined number of phototransistors to block their reception of light and eliminate false detections due to edge wander. However, this shielding process also blocks the system's ability to detect separated edge cracks on products with wandering edges. Finally, as with the other systems, this type of system is also completely ineffective at detecting non-separated edge cracks.

There is, therefore, a need in the art to provide a method and apparatus for detecting both separated and non-separated edge cracks on various types of travelling products without encountering these and other types of problems.

SUMMARY OF THE INVENTION

Briefly described, the present invention includes a method for detecting both separated and non-separated edge cracks on a travelling product, such as a continuous paper web, and the like, and an apparatus for performing the invented method. The steps of the invented method include directing air onto a travelling product with sufficient force to separate non-separated edge cracks in the travelling product and utilizing an optical signal device to detect edge cracks in the travelling product.

In its preferred embodiment, the present invention includes directing two streams of air toward opposite surfaces of the travelling product to effectively separate the non-separated edge cracks. The optical signal device includes an optical signal emitter and an optical signal receiver. Each of these devices are positioned to face opposite surfaces of the travelling product and oriented so that the direction of the emitted optical signals forms an angle other than a right angle with the direction in which the product is travelling. In this arrangement, the optical signals which are emitted from the optical signal emitter are obstructed by non-cracked portions of the travelling product but pass through even slightly separated edge cracks to be received by the optical signal receiver. Receipt of optical signals by the optical signal receiver provides indications of edge cracks.

The air used to separate the non-separated cracks is also directed across the optical signal emitter and the optical signal receiver to prevent the build-up of foreign particles, thus improving the integrity of the method. The method also involves automatically tracking the edge of the travelling product and moving the optical sensing device along with the edge of the travelling product so that the optical signal device is continuously positioned at a predetermined distance from the edge of the product.

The preferred embodiment of the present invention includes an air-purged housing and an optical sensor located within the air-purged housing. The air-purged housing includes an inner air chamber into which an air receipt port and two air delivery ports have access. The air receipt port is connected to an air supply, such as an air compressor. The two air delivery ports are appropriately located to direct two oppositely directed air streams at opposite surfaces of the travelling product to separate non-separated edge cracks. The air-purged housing is connected to a linear actuator which cooperates with an attached edge tracker to maintain the air-purged housing in a constant position relative to the edge of the travelling product. A control panel and an output device are also connected to keep track of the number of detected edge cracks and to provide selective manual control of the positioning of the air-purged housing.

In this preferred embodiment, the optical sensor is a photoelectric device and includes a control element connected to an optical signal emitter and to an optical signal receiver through transmission media. Each of these elements are located within the inner air chamber of the air-purged housing. In alternate embodiments, the optical sensor is a fiber optic device, air hoses internal to the air-purged housing are included, the control element and portions of the transmission media are external to the air-purged housing, and the apparatus includes two separate housings which define two separate inner air chambers. In still another embodiment, only an optical sensor, air supply devices, and support structures are included without an air-purged housing.

In another alternate embodiment of the present invention, only one stream of air is directed toward the travelling product to separate the non-separated cracks. The optical signal device includes an optical transceiver device which transmits and receives optical signals. Non-cracked portions of the travelling product reflect transmitted optical signals which are received by the optical transceiver device. Cracks are detected because they do not reflect the transmitted optical signals.

This alternate embodiment of the present invention includes an air-purged housing and an optical sensor located within the air-purged housing. This apparatus is similar to the preferred embodiment of the present invention. However, the air-purged housing in this alternate embodiment includes an inner air chamber into which an air receipt port and only one air delivery port have access. Furthermore, the optical sensor includes an optical transceiver which transmits and receives optical signals. In a last embodiment, an optical sensor is located within an air-sealed housing which provides a transparent viewing area through which optical signals may traverse through the housing. An air delivery device cooperates with an air-deflection device located adjacent to the viewing area in continuously directing air across the view area to improve the integrity of the method and directing air toward the travelling product to separate non-separated edge cracks.

It is therefore an object of the present invention to provide a method for detecting both separated and non-separated edge cracks on a travelling product, such as a continuous paper web, and the like.

Another object of the present invention is to provide an apparatus for detecting both separated and non-separated edge cracks on a travelling product, such as a continuous paper web, and the like.

Another object of the present invention is to provide a method for detecting edge cracks in travelling products which includes directing air onto a travelling product with sufficient force to separate non-separated edge cracks in the travelling product and utilizing an optical signal device to detect edge cracks in the travelling product.

Yet another object of the present invention is to provide a method for detecting edge cracks in travelling products which includes directing two streams of air toward opposite surfaces of the travelling product to effectively separate the non-separated edge cracks and utilizing an optical signal device to detect edge cracks in the travelling product.

Still another object of the present invention is to provide a method for detecting edge cracks in travelling products which includes positioning an optical signal emitter and an optical signal receiver to face opposite surfaces of the travelling product and orienting the devices so that the direction of the emitted optical signals forms an angle other than a right angle with the direction in which the product is travelling.

Still another object of the present invention is to provide a method for detecting edge cracks in travelling products which also provides for directing air across an optical signal emitter and an optical signal receiver to prevent the build-up of foreign particles, thus improving the integrity of the method.

Still another object of the present invention is to provide a method for maintaining an optical sensor systems which includes directing air across an optical signal emitter and an optical signal receiver to prevent the build-up of foreign particles, thus improving the integrity of the method.

Still another object of the present invention is to provide a method for detecting edge cracks in travelling products which includes automatically tracking the edge of the travelling product and moving an optical sensing device along with the edge of the travelling product so that the optical signal device is continuously positioned at a predetermined distance from the edge of the product.

Still another object of the present invention is to provide an apparatus for detecting edge cracks in a travelling product which includes an air-purged housing and a photoelectric optical sensor located within the air-purged housing.

Still another object of the present invention is to provide an optical sensing apparatus which includes an air-purged housing and a photoelectric optical sensor located within the air-purged housing.

Still another object of the present invention is to provide an apparatus for detecting edge cracks in a travelling product which includes an air-purged housing which includes two air delivery ports which are appropriately located to direct two oppositely directed air streams at opposite surfaces of the travelling product to separate non-separated edge cracks.

Still another object of the present invention is to provide an apparatus for detecting edge cracks in a travelling product which includes an air-purged housing connected to a linear actuator which cooperates with an attached edge tracker to maintain the air-purged housing in a constant position relative to the edge of the travelling product.

Still another object of the present invention is to provide an apparatus for detecting edge cracks in a travelling product which includes an air-purged housing and a fiber optic sensing device which includes a control element and transmission media located, at least partially, external to the air-purged housing.

Still another object of the present invention is to provide an optical sensing apparatus which includes an air-purged housing and a fiber optic sensing device which includes a control element and transmission media located, at least partially, external to the air-purged housing.

Still another object of the present invention is to provide an apparatus for detecting edge cracks in a travelling product which includes at least two separate air-purged housings which define two separate inner air chambers.

Still another object of the present invention is to provide a method for detecting edge cracks in travelling products which includes directing one stream of air toward a travelling product to separate the non-separated edge cracks in the travelling product and utilizing an optical signal device which includes an optical transceiver which transmits and receives optical signals.

Still another object of the present invention is to provide a method for detecting edge cracks in travelling products which includes directing optical signals which are reflected by non-cracked portions of a travelling product and are not reflected by cracked portions of a travelling product.

Still another object of the present invention is to provide an apparatus for detecting edge cracks in travelling products which includes an air-purged housing which includes an inner air chamber into which an air receipt port and one air delivery port have access and wherein an optical signal device is located.

Still another object of the present invention is to provide an optical sensor system which includes an air-purged housing which includes an inner air chamber into which an air receipt port and one air delivery port have access and wherein an optical sensing device is located.

Still another object of the present invention is to provide an apparatus for detecting edge cracks in travelling products which includes an air-sealed housing which provides a transparent viewing area through which optical signals may traverse through the housing and an air delivery device which cooperates with an air-deflection device located adjacent to the viewing area to continuously direct air across the viewing area to improve the integrity of the method and to direct air toward the travelling product to separate non-separated edge cracks.

Other objects, features and advantages of the present invention will become apparent upon reading and understanding the present specification, when taken in conjunction with the accompanying drawings.

DETAILED DESCRIPTION OF THE PREFERRED EMBODIMENT

Figure 1:
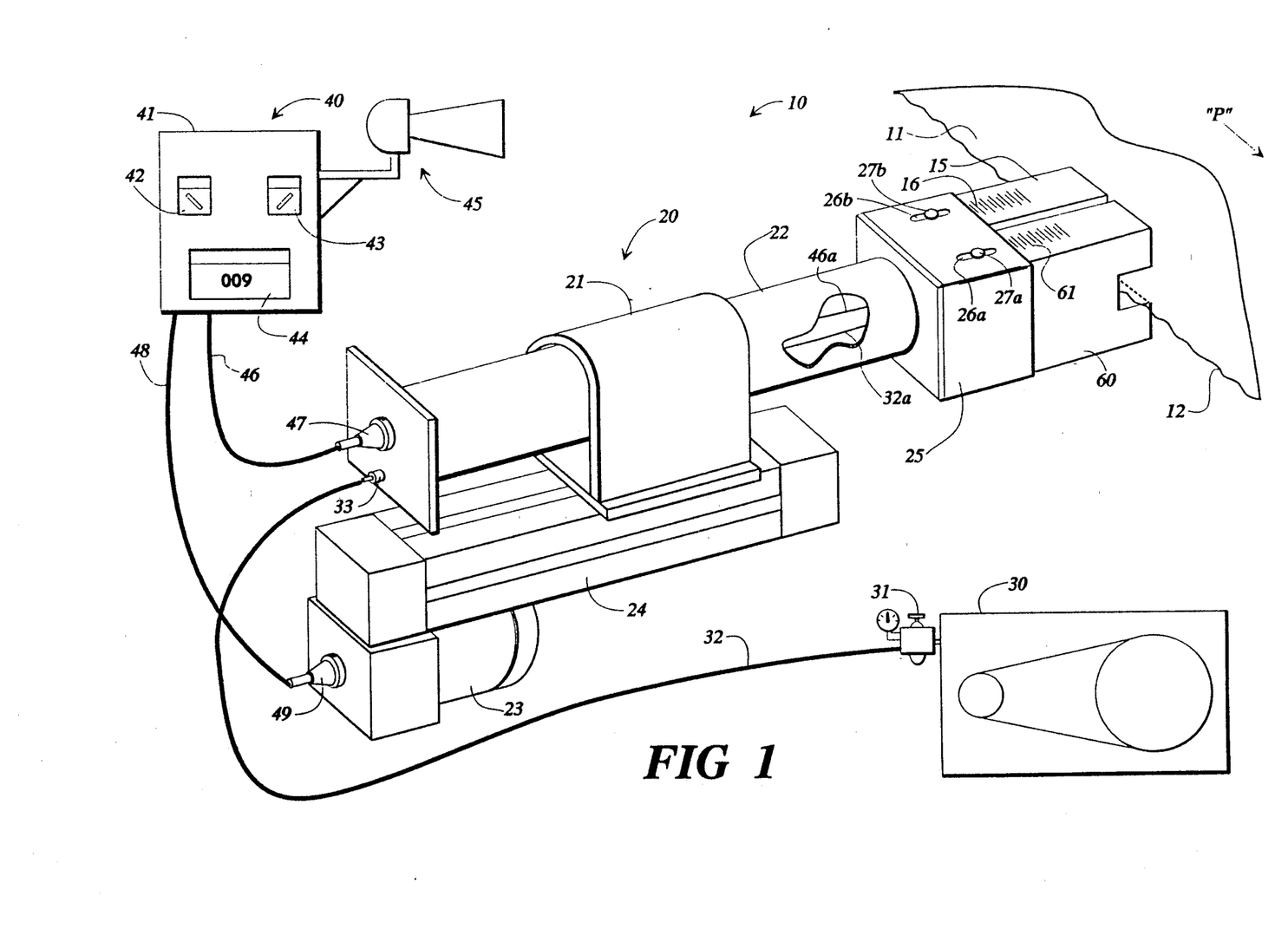
FIG. 1 is a pictorial view of a preferred embodiment of an edge crack detector in accordance with the preferred embodiment of the present invention and a portion of a travelling product.

Referring now in greater detail to the drawings in which like numerals represent like components throughout the several views, FIG. 1 shows a pictorial view of a preferred embodiment of an edge crack detector 10 in accordance with the preferred embodiment of the present invention and a portion of a travelling product 11. Examples of acceptable travelling product 1 include: continuous paper webs, sheet metal, plastic, fabric, and other travelling products. Edge follower module 15 and detector module 60 are seen monitoring product edge 12 of product 11. Both Edge follower module 15 and detector module 60 are connected to module housing 25 by module housing slots 26a and 26b and module housing set screws 27a and 27b. Edge follower alignment marks 16 and detector module alignment marks 61 are seen as part of edge follower module 15 and detector module 60, respectively.

Linear actuator 20 includes module housing 25, actuator arm 22, actuator sleeve 21, actuator base 24, and actuator motor 23. Module housing 25 is seen rigidly connected to actuator arm 22. Actuator sleeve 21 is connected around actuator arm 22 in such a manner that actuator sleeve 21 may be selectively loosened to allow actuator arm 22 to move relative to actuator sleeve 21. Actuator sleeve 21 includes a lower nut mechanism which is threaded around a long screw mechanism located within actuator housing 24 and driven by actuator motor 23. The specific internal design of a linear actuator such as linear actuator 20 is considered known within the industry and, therefore, not shown in detail in the drawings. One example of an acceptable linear actuator is available from Industrial Device Corp. of Novato, Calif. as product number RD355B-12-MS5-MC-Q1.

Control unit 40 includes control panel 41 and output horn 45. Control panel 41 includes an auto/manual switch 42, an in/out switch 43, and a crack counter 44. Module signal carrier 46 and actuator motor line 48 connect control unit 40 to linear actuator 20. Actuator motor line 48 is connected to actuator motor 23 through actuator motor coupling 49. Module signal carrier 46 is connected to actuator signal coupling 47 which is connected to hollow actuator arm 22. Arm carrier 46a is threaded through actuator arm 22 and connected between actuator signal coupling 47 and both edge follower module 15 and detector module 60. Air source 30 supplies air which is regulated by regulator 31 through air supply hose 32 to actuator air coupling 33. Arm hose 32a is threaded through actuator arm 22 to connect to edge follower module 15 and detector module 60.

A general description of relevant aspects of the operation of the preferred embodiment of edge crack detector 10 will now be described. Edge follower module 15, through techniques considered well-known in the industry, tracks the wander of the product edge 12 as product 11 moves along in the production process in the direction indicated by arrow "P". It should be understood that an arrangement in which the relative positions of edge follower module 15 and detector module 60 are reversed, ie., product 11 is in effect travelling in a direction opposite to that indicated by arrow "P", is also an arrangement considered to be within the scope of the present invention. Edge follower module 15 and detector module 60 may both easily be removed from module housing 25 for replacement or repair. This modular construction of the present invention is considered to be one of the many novel features of the present invention.

Edge follower module 15 continually generates signals which indicate its position relative to the wandering product edge 12. These signals are transferred to control unit 40 through arm carrier 46a, actuator signal coupling 47, and module signal carrier 46. If auto/manual switch 42 is set to allow automatic operation of edge crack detector 10, control unit 40 responds to these signals by effecting operation of actuator motor 23. As signals from edge follower module 15 indicate that product edge 12 has wandered in or out from an optimum relative position, actuator motor 23 is caused to effect linear movement of actuator sleeve 21 to "follow" product edge 12. Because actuator arm 22, module housing 25, edge follower module 15, and detector module 60 are all connected to actuator sleeve 21, they are also moved in the direction which follows product edge 12. As edge follower module 15 reaches the optimum position relative to product edge 12, movement ceases.

In certain applications, auto/manual switch 42 is set in the manual position so that linear movement is not automatic. Such applications include, for example, circumstances where there is no wander in product edge 12, where it is desirable to only detect cracks along a predefined line, or during initialization of the present invention. When auto/manual switch 42 is set in the manual position, in/out switch 43 may be used to manually control actuator motor 23. Throughout the remainder of this description, auto/manual switch 42 is considered to be in the automatic position so that the position of detector module 60 relative to product edge 12 remains constant as determined by the relationship between follower alignment marks 16 and detector alignment marks 61. This relationship determines how deeply into product 11 and away from product edge 12 detector module 60 monitors.

As detector module 60 detects edge cracks in product 11, the details of which are discussed below, signals are generated and transmitted to control unit 40 through arm carrier 46a and its related components. Crack counter 44 counts the number of cracks detected by detector module 60, and horn 45 provides audible output of each detection. In other embodiments, alternative output devices, such as a notification light or an edge marker mounted on module housing 25, are used to provide visual notification of an edge crack in product 11.

Air supply 30 continuously supplies air to detector module 60 throughout the entire process. Air regulator 31 maintains a constant velocity of air flow within air supply hose 32. One example of an acceptable air supply 30 is a common air compressor. The exact use of air provided by air supply 30 is discussed in detail below.

Figure 2:
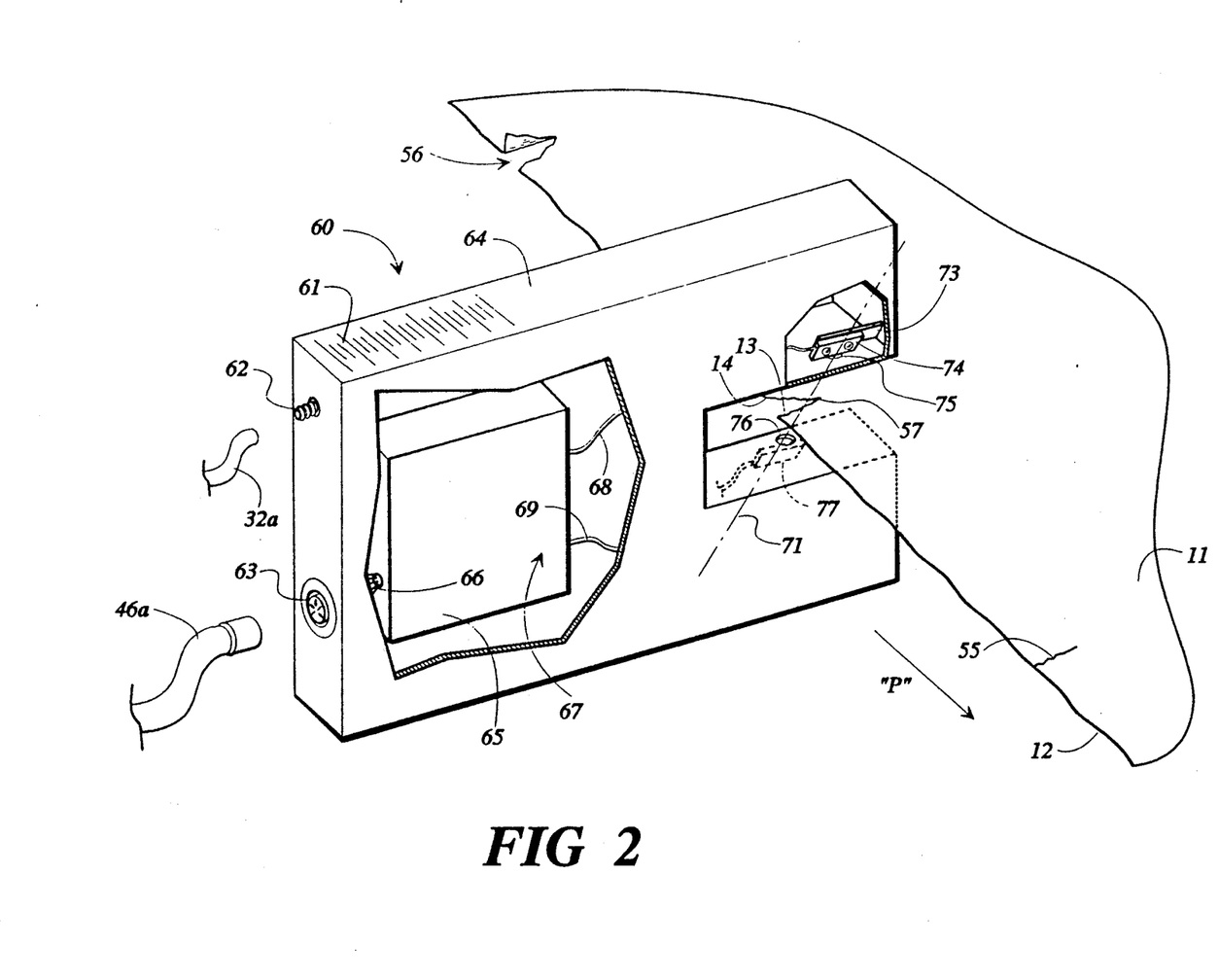
FIG. 2 is a perspective view of a detector module of the preferred embodiment of the present invention with parts cut away for clarity and a portion of a travelling product.

Referring now to FIG. 2, a perspective view of the detector module 60 with parts cut away for clarity and a portion of travelling product 11 is shown. Arm hose 32a is shown adjacent to detector air intake coupling 62, one example of an air receipt port which provides an opening through detector housing 64. Arm hose 32a is normally connected to detector air intake coupling 62 so that air is supplied into an internal air chamber formed by detector module 60. The shape of detector housing 64 shown in FIG. 2 is only one example of an acceptable detector housing shapes. Various other shapes are also considered within the scope of the present invention.

Detector signal coupling 63 is shown adjacent to arm carrier 46a. These two elements are also normally connected together. Internal to detector housing 64 is optical sensor 67 which consists of controller conductors 66, photoelectric signal controller 65, transmitter conductor 68, receiver conductor 69, photoelectric transmitter 74 and photoelectric receiver 77, represented with dotted lines. Acceptable examples of these components include the PS52 sensors and PS2-61 amplifier manufactured by Keyence Corp. of America, of Fair Lawn, N.J. Controller conductors 66 proceed from detector signal coupling 63 to photoelectric signal controller 65. Transmitter conductor 68 and receiver conductor 69 are also connected to photoelectric signal controller 65. Transmitter conductor 68 extends between photoelectric signal controller 65 and photoelectric transmitter 74. Receiver conductor 69 extends between photoelectric signal controller 65 and photoelectric receiver 77, represented by dotted lines.

Photoelectric transmitter 74 is connected to detector housing 64 through transmitter support 73. Transmitter air outlet 75 is also seen below photoelectric transmitter 74. Transmitter air outlet 75 is an opening in detector housing 64 through which air flows and through which optical signals emitted from photoelectric transmitter 74 may travel. Receiver air outlet 76 is also seen as an opening in detector housing 64. Photoelectric receiver 77 is seen below receiver air outlet 76 and understood to be connected to detector housing 64 in a manner similar to that of photoelectric transmitter 74. Line of sight 71 is also seen extending from photoelectric transmitter 74, passing through transmitter air outlet 75 and receiver air outlet 76, and contacting photoelectric receiver 77.

Product 11 is seen travelling in the direction as indicated by arrows "P". Separated crack 56 and non-separated crack 55 are seen located near product edge 12. Located just above receiver air outlet is forced crack 57 which is defined by leading crack surface 13 and trailing crack surface 14.

A general discussion of the operation of detector module 60 is disclosed in more detail above. In summary, the overall purpose of detector module 60 is to detect all types of edge cracks in product 11 and transmit signals along arm carrier 46a which represent the detection of such edge cracks. Air is continuously supplied through detector air intake coupling 62 into detector housing 64 which is air-tight except for transmitter air outlet 75 and receiver air outlet 76. Air is directed through detector housing 64 for at least two purposes.

A first purpose of the air flow is to continuously purge detector housing 64 of all dust and other obstructions which would tend to degrade the integrity of the detection method of the present invention. Air flows continuously across photoelectric transmitter 74 and photoelectric receiver 77 as it exits through transmitter air outlet 75 and receiver air outlet 76. The entire spaces between these photoelectric devices and their respective air outlets are continuously purged with air to prevent foreign particles located outside detector housing 64 from entering the air-purged detector housing 64.

A second purpose of the air flow involves separating non-separated edge cracks. During the time in which a non-separated crack, one example of which is shown as non-separated crack 55, travels between transmitter air outlet 75 and receiver air outlet 76, the crack is forced open by the two air streams flowing from transmitter air outlet 75 and receiver air outlet 76. Forced crack 57 shows the results of this air flow. Air is directed down onto leading crack surface 13 from transmitter air outlet 75 while air is being directed upward onto trailing crack surface 14. This combination of oppositely directed air streams onto opposite sides of product 11 at points displaced along the direction of travel of product 11 is considered one of the many unique aspects of the present invention. A detectable separation is thereby created in a normally non-separated crack. Because no element of the present invention actually physically contacts product 11, the invented method is non-intrusive and not prone to disrupt the process. For another view of product 11, refer to FIG. 7.

Referring back to FIG. 2, the separation is detected by optical sensor 67. Electrical impulses are generated by photoelectric signal controller 65 and communicated through transmitter conductor 68, which acts as a transmission medium, to photoelectric transmitter 74. Photoelectric transmitter 74 acts as a transducer to convert the received electrical impulses into optical signals. These optical signals are transmitted along line of sight 71 and through transmitter air outlet 75.

These optical signals are then normally intercepted and absorbed by non-cracked portions of product 11. As a crack in product 11 passes through line of sight 71, optical signals emitted from photoelectric transmitter 75 travel through the crack and are received by photoelectric receiver 77. Photoelectric receiver 77 also functions as a transducer. However, it converts this received optical energy into electrical impulses and sends them along receiver conductor 69 to photoelectric signal controller 65. Additional signals are then generated by photoelectric signal controller 65 and transmitted along controller conductors 66 and out into arm carrier 46a.

The angular positioning of photoelectric transmitter 74 and photoelectric receiver 77 is also considered one of the many unique aspects of the present invention both an element in combination with the process of directing air toward product 11 and as a separate inventive aspect of the present invention. (ie. without the direction of air toward product 11) By attaching photoelectric transmitter 74 and photoelectric receiver 77 to detector housing 64 in the angled orientation shown, line of sight 71, and thus the direction in which optical signals are emitted, forms an angle other than a right angle with the direction in which product 11 is travelling.

This angled signal path enables detector module 60 to detect cracks which are only slightly separated. In fact, many cracks which are only slightly separated are not visible from a line of sight which forms a right angle, substantially, with the direction in which product 11 is travelling. An angled line of sight 71 enables optical sensor 67 to detect a larger number of edge cracks. Also, this angled line of sight enhances the integrity of the present method in processes which produce product 11 at very high speeds and those which produce a very stiff product 11 which only separates slightly, if any, in response to air pressure. It should also be very clear that separated crack 56 will also be easily detected by optical sensor 67.

It is important to note the existence of a relationship between certain parameters of the present invention. The first parameter is the distance along the direction in which product 11 travels between transmitter air outlet 75 and receiver air outlet 76. The second parameter is the angle between the direction in which optical signals are emitted from photoelectric transmitter 74 and the direction in which product 11 travels. It is often desirable to make the second parameter as small as possible so that the smallest of separations may be detected. (ie., line of sight 71 becomes nearly parallel to the direction in which product 11 travels). However, reduction of this angle normally entails increasing the first parameter, the distance between the outlets. As this parameter increases, the two air streams which flow through transmitter air outlet 75 and receiver air outlet 76 become spaced further apart. Consequently, less force is applied to product 11 in the areas most adjacent to the actual crack. This reduction in useful force tends to reduce the amount of separation. A unique balance between these two parameters which depends on several factors, including the speed at which product 11 travels, as well as the stiffness of product 11, is necessary to achieve the optimum results.

The design of detector housing 64 with respect to the amount of surface area adjacent to photoelectric transmitter 74 and photoelectric receiver 77 is another of the many important aspects of the preferred embodiment of the present invention. To decrease interference by outside light sources with the reception of optical signals received by photoelectric receiver 77, detector housing 64 is designed to, at least partially, shadow this area. Although, in the preferred embodiment, pulsed light is emitted from photoelectric transmitter 74, the emission of continuous light is considered within the scope of the present invention. It is considered to be well known that pulsed light is less susceptible to interference from external light sources, yet a very rapidly travelling product 11 may require continuous light. Regardless of which light is used, this shading feature reduces interference by outside light sources.

Figures 3, 4:
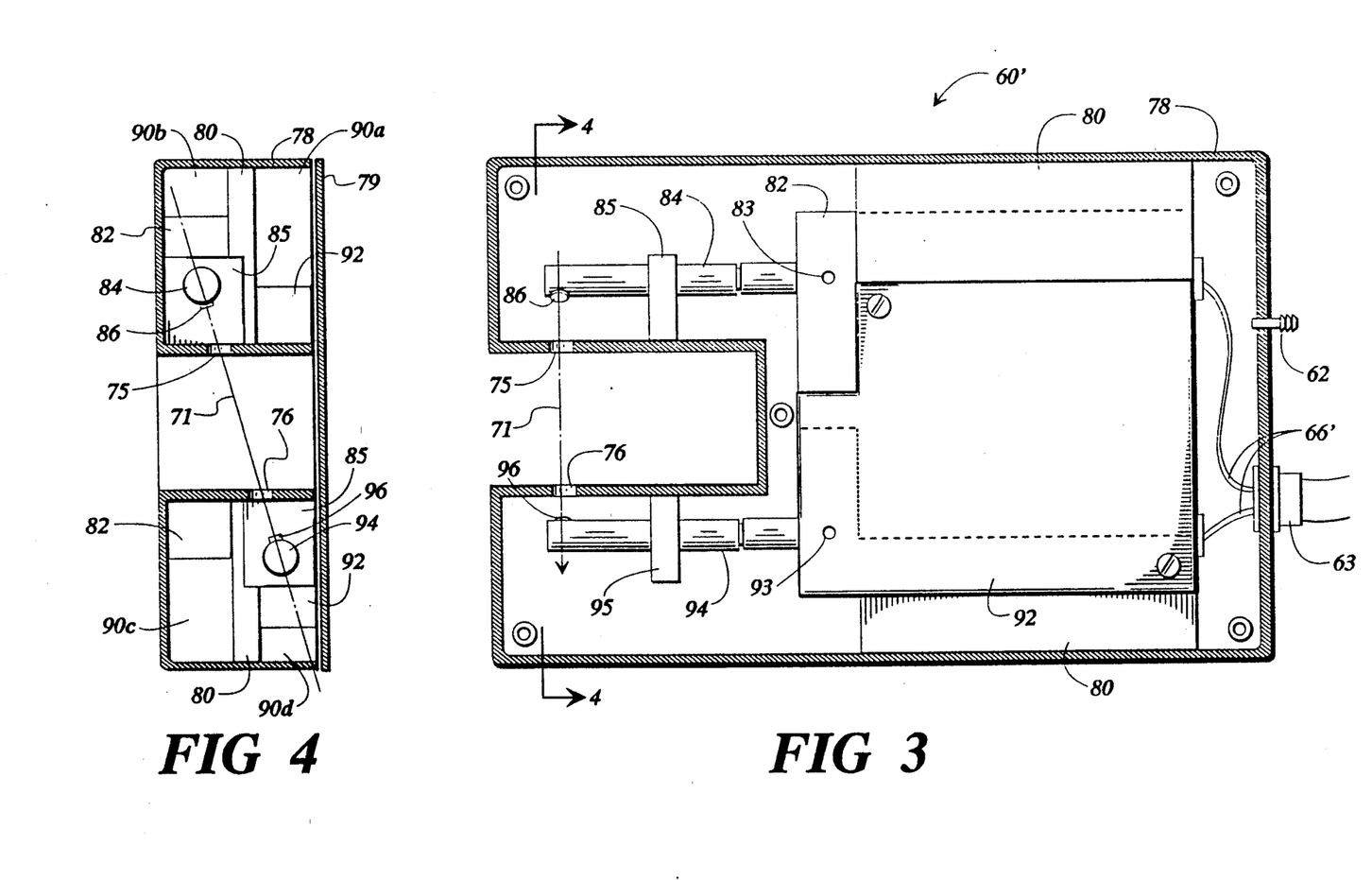
FIG. 3 is a side view of a detector module of a second embodiment of the present invention shown with the cover plate removed.
FIG. 4 is a sectional view of the detector module of FIG. 3 taken along the line indicated by arrows "A".

Referring now to FIGS. 3 & 4, FIG. 3 shows a side view of detector module 60', of a second embodiment of the present invention shown with a cover plate removed, and FIG. 4 shows a sectional view of detector module 60' taken along the line indicated by arrows "A" shown adjacent to module cover plate 79. The structure and operation of this second embodiment of the present invention are very similar to those of the preferred embodiment.

In FIG. 3, detector air intake coupling 62 and detector signal coupling 63 are seen connected though module lower section 78 of detector module 60'. Structural insert 80 is connected to module lower section 78 as shown in both FIG. 3 and FIG. 4. This connection may be accomplished through spot welding or screwing through module lower section 78. Fiber transmitter controller 82 and fiber receiver controller 92 are connected to each side of structural insert 80 as is shown. The dotted lines in FIG. 3 represent the outline of fiber transmitter controller 82. Controller conductors 66' connect fiber transmitter controller 82 and fiber receiver controller 92 to detector signal coupling 63. FIG. 4 reveals four open areas 90a-90d. These are areas through which air is free to flow.

Transmitter fiber 84 is connected to fiber transmitter controller 82 in conjunction with transmitter set screw 83 which determines whether transmitter fiber 84 is free to rotate so that transmitter fiber 84 may be aligned properly. Similarly, receiver fiber 94 is connected to fiber receiver controller 92 in conjunction with receiver set screw 93 which functions similarly. Transmitter fiber support 85 is connected to module lower section 78 and supports transmitter fiber 84. Similarly, receiver fiber support 95 is connected to module lower section 78 and supports receiver fiber 94.

Transmitter fiber ending 86 is shown in an orientation in which optical signals emitted from transmitter fiber ending 86 pass through transmitter air outlet 75 along line of sight 71. If these signals are not obstructed while outside the inner air chamber of detector module 60', they pass through receiver air outlet 76 and are received by a similarly oriented receiver fiber ending 96. Transmitter fiber support 85 and receiver fiber support 95 are preferably slotted so that transmitter fiber 84 and receiver fiber 94 are properly oriented upon insertion into the corresponding support. Acceptable examples of these fiber components include the SM53EFO and SM53RFO sensor pair and IA1.53PMTA fiber optic cables from Banner Engineering Corp. of Minneapolis, Minn.

Both transmitter fiber ending 86 and receiver fiber ending 96 are preferably off-center from transmitter air outlet 75 and receiver air outlet 76, respectively. In addition to allowing angled line of sight 71 through the respective air outlets 75, 76, this arrangement tends to assist in keeping the fiber endings 86, 96 clean. That is, falling debris, such as ink or wet product, which is not repelled by the exiting air flow and which falls vertically through air outlets 75, 76, would tend to fall past fiber endings 86, 96.

Figure 5:
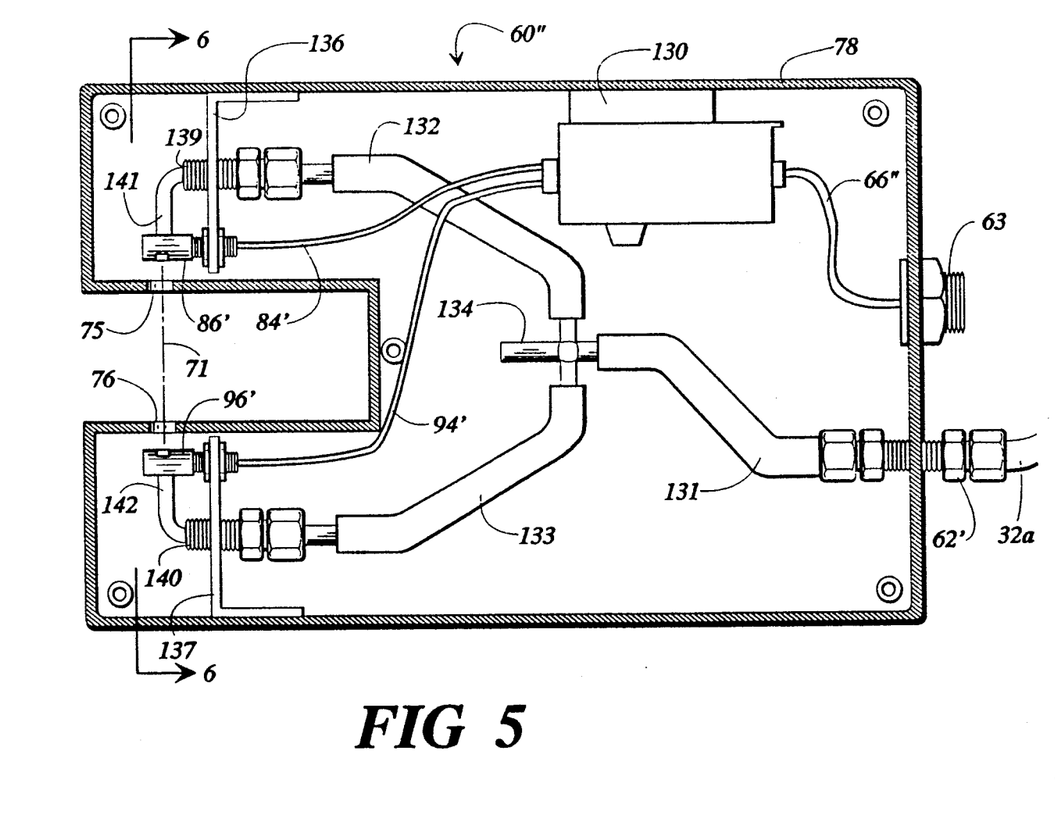
FIG. 5 is a side view of a detector module of a third embodiment of the present invention shown with the cover plate removed.
Figure 6:
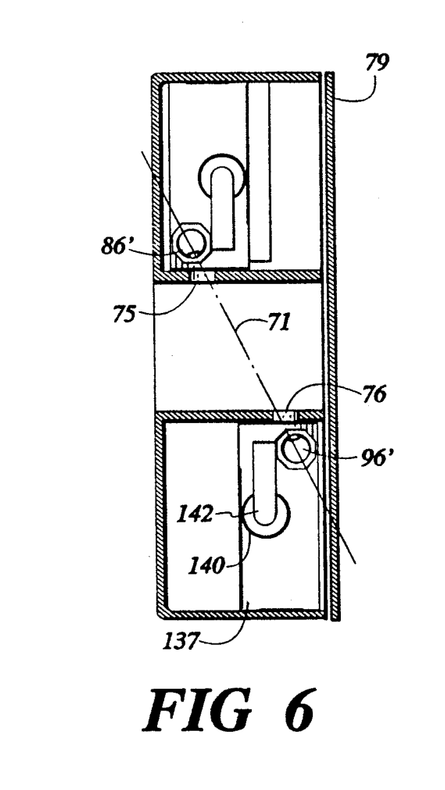
FIG. 6 is a sectional view of the detector module of FIG. 5 taken along the line indicated by arrows "B".

Referring now to FIGS. 5 and 6, FIG. 5 shows a side view of detector module 60" of a third embodiment of the present invention shown without a cover plate, and FIG. 6 shows a sectional view of detector module 60" taken along the line indicated by arrows "B". Once again, the structure and operation of this third embodiment of the present invention are very similar to those of the preferred embodiment.

Module lower section 78 and module cover plate 79 are very similar to those shown in FIGS. 3 and 4. Once again, fiber optic devices are used. Controller conductor 66" connects detector signal coupling 63 to fiber controller 130 which is connected to module lower section 78. Transmitter fiber 84' and receiver fiber 94' connect fiber controller 130 to transmitter bracket 136 and receiver bracket 137, respectively. Transmitter fiber ending 86' and receiver fiber ending 96' are also connected to transmitter bracket 136 and receiver bracket 137, respectively. As before, these fiber endings are located off-center from the corresponding air outlets. The operation of the light components is similar to that discussed above. Acceptable examples of the light components include the FS2-65 controller and FU7F w/F-1 cables from Keyence Corp. of America, of Fair Lawn, N.J.

Some of the most obvious additions represented by this alternate embodiment of the present invention are internal air hoses. Internal supply hose 131 is connected to detector air intake coupling 62' and receives air from arm hose 32a. Internal supply hose 131 is connected to air bridge 134 which is connected to internal transmitter hose 132 and internal receiver hose 133. Air bridge 134 also has another opening out into the internal air chamber of detector module 60". Depending on the environment and available air pressure, the size of this opening may be varied to change the amount of air which exits into the internal air chamber.

Transmitter air coupling 139 connects internal transmitter hose 132 to transmitter bracket 136 and transmitter air spout 141. Similarly, receiver air coupling 140 connects internal receiver hose 133 to receiver bracket 137 and receiver air spout 142. Transmitter air spout 141 directs air toward transmitter air outlet 75, and receiver air spout 142 directs air toward receiver air outlet 76. As before, two streams of air exit transmitter air outlet 75 and receiver air outlet 76. Also, as shown in FIG. 6, air which exits from transmitter air spout 141 and receiver air spout 142 also rushes past transmitter fiber ending 86' and receiver fiber ending 96', respectively. The spaces between the fiber endings and the air outlets are again continuously purged of obstructions.

In some circumstances, such as those involving stiff travelling products, air must exit detector module 60" at a high velocity. This alternate embodiment provides this capability without the need for large, if any, increases in the air pressure entering detector module 60" through detector air intake coupling 62' By directing the air through this hose network, a lower pressure is required going into detector module 60" to achieve the same velocity of air exiting transmitter air outlet 75 and receiver air outlet 76.

Figure 7:
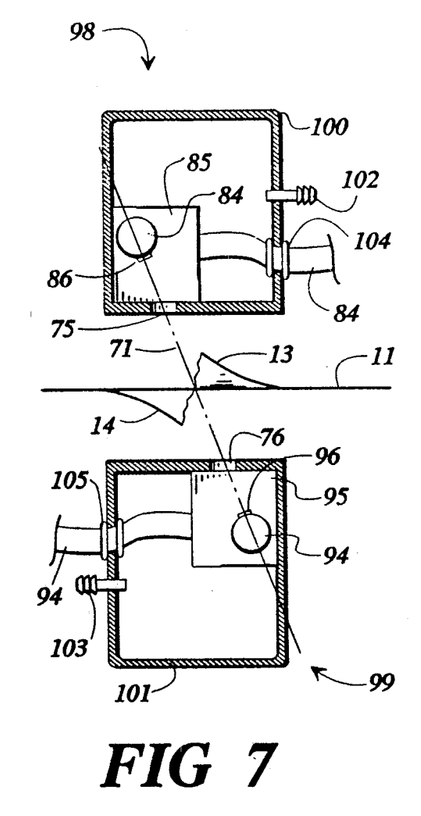
FIG. 7 is an end view of two detector modules of a fourth embodiment of the present invention and a portion of a travelling product.

Referring now to FIG. 7, an end view of two detector modules of a fourth embodiment of the present invention and a portion of a travelling product 11 are seen. In this embodiment, each of these modules are generally cube-shaped for ease of construction and mounting. However, various other shapes are also considered within the scope of the present invention. Certain aspects of this alternate embodiment are similar to embodiments discussed above, yet there are aspects which are very different.

Transmitter assembly 98 is seen above product 11, and receiver assembly 99 is seen below product 11. Transmitter air intake 102 provides an opening into an air chamber created by transmitter housing 100, and receiver air intake 103 provides an opening into receiver housing 101. Transmitter fiber 84 travels through transmitter housing 100 and is secured by transmitter grommet 104; likewise, receiver fiber 94 travels through receiver housing 101 and is secured by receiver grommet 105. Transmitter fiber 84 is also supported and oriented by transmitter fiber support 85; similarly, receiver fiber 94 is also supported and oriented by receiver fiber support 95.

As discussed above, air is directed out of transmitter air outlet 75 and receiver air outlet 76 to deflect trailing crack surface 14 and leading crack surface 13, respectively. The air is also used to purge transmitter housing 100 and receiver housing 101. Furthermore, optical signals are emitted from transmitter fiber ending 86 along line of sight 71 through transmitter air outlet 75 and, assuming no obstructions, through receiver air outlet 76 to be received by receiver fiber ending 96.

In this alternate embodiment, two separate housings are shown. The use of two separate housings provides additional versatility. The angle of line of sight 71 can be readily altered through various positioning of the housings, and the distance of each housing to product 11 can be varied. In addition, for products 11 which bend more readily in one direction, not only can the distances between product 11 and each different housing be altered independently, the air pressure into each housing can be varied.

Also, in this alternate embodiment, a signal controller is not located within either of the housings. With regard to the optical elements, only portions of fibers and fiber endings are located within the housings. More control is now possible from a remote location. Optical sensors typically have several options which are set from the controller, such as whether light or darkness is the steady state, whether a delay will be placed on the output, or whether the sensitivity is high or low. Without a delay on the output, the size of the crack could be determined. These options may be controlled remotely with this alternate embodiment. It should also be understood to be within the scope of the present invention that the signal controllers shown within housings of other embodiments could also be located outside those housings.

Figure 8:
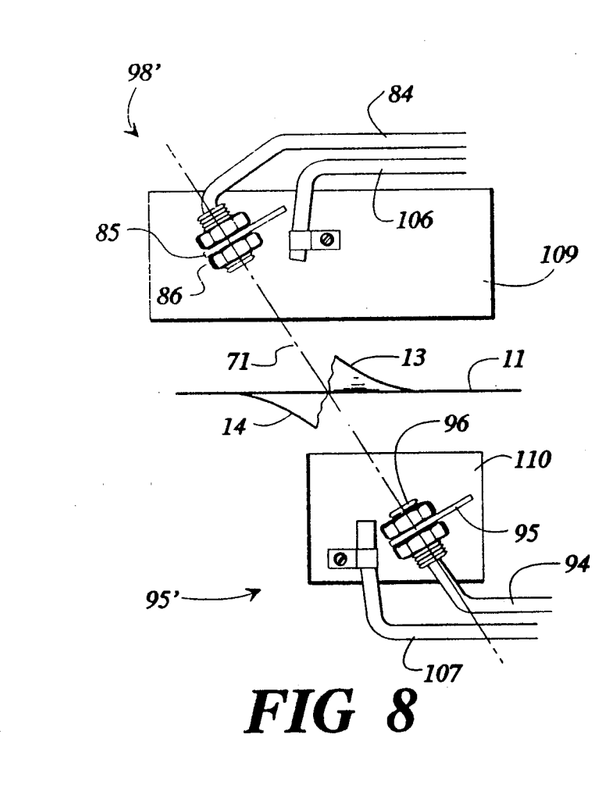
FIG. 8 is an end view of an open detector assembly of a fifth embodiment of the present invention and a portion of a travelling product.

Referring now to FIG. 8, an end view of an open detector assembly of a fifth embodiment of the present invention and a portion of a travelling product 11 is shown. This embodiment of the present invention differs from previously discussed embodiments in that no housing is included. Transmitter assembly 98' is located above product 11, and receiver assembly 99' is located below product 11. Air is supplied through transmitter air supply 106 and receiver air supply 107 which are connected to transmitter assembly support 109 and receiver assembly 110, respectively. Transmitter fiber 84 is connected to transmitter assembly support 109 through transmitter fiber support 85 which also supports transmitter fiber ending 86. Receiver fiber 94 is connected to receiver assembly support 110 through receiver fiber support 95 which also supports receiver fiber ending 96.

As with the preceding embodiment disclosed in FIG 7, two separate assemblies are included. All of the advantages discussed above with respect to the use of separate structure are also included with this alternate embodiment. Furthermore, the method of directing air through air supplies such as transmitter air supply 106 and receiver air supply 107 is discussed with reference to the embodiment disclosed in FIG. 5 above. As air exits each of these supplies, is travels across transmitter fiber ending 86 and transmitter fiber ending 96 to continuously clean these fiber endings. The air also impacts product 11 so that leading crack surface 13 and trailing crack surface 14 are separated, as discussed above.

Figure 9:
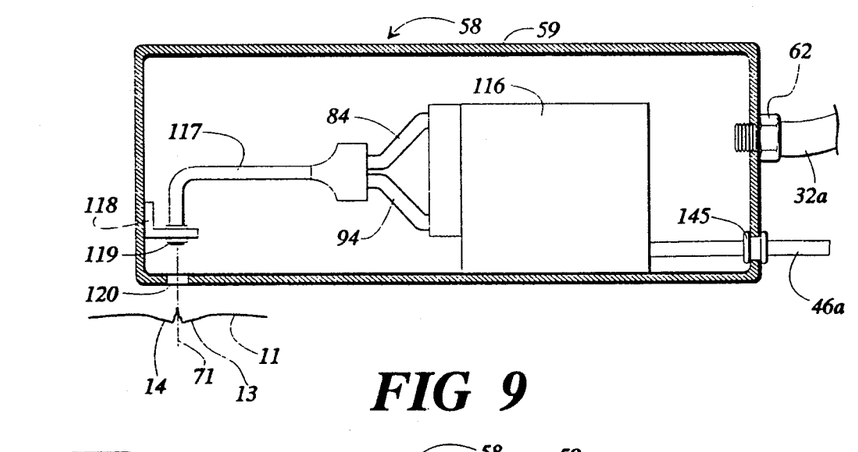
FIG. 9 is a side view of a reflection detector module of a sixth embodiment of the present invention and a portion of a travelling product.

Referring now to FIG. 9, a side view of a reflection detector module of a sixth embodiment of the present invention and a portion of a travelling product are shown. In this embodiment, reflection housing 59 is substantially shown as a rectangular box. This shape is relatively easy to construct and facilitates mounting. However, various other shapes are also considered within the scope of the present invention.

Arm hose 32a is seen supplying air through detector air intake coupling 62 into an air chamber created by reflection housing 59. Arm carrier 46a travels through an opening in reflection housing 59 which is sealed by fiber grommet 145 and is connected to transceiver controller 116 located within reflection housing 59. Transmitter fiber 84 and receiver fiber 94 proceed from transceiver controller 116 and are connected to bifurcated fiber 117 which contains at least two separate signal carrier paths. Signals may travel within bifurcated fiber 117 in opposite directions without interfering with each other. Transceiver support 118 supports bifurcated fiber 117 and bifurcated fiber ending 119 which is positioned above transceiver air outlet 120 and aligned with line of site 71. Acceptable examples of the sensor elements include the SM512LBFO controller and BAT235 fiber from Banner Engineering Corp. of Minneapolis, Minn.

Air is continuously directed through air outlet 120 to continuously purge reflection housing 59 and separate non-separated edge cracks, such as that represented by leading crack surface 13 and trailing crack surface 14. A single stream of air causes product 11 to bend away from reflection detector module 58 so that non-separated cracks become at least slightly separated. This method of employing only one stream of air is very useful in environments where it is only possible, or desirable, to place detector components on one side of product 11.

Optical signals are emitted from bifurcated fiber ending 119 along line of sight 71 to travel through transceiver air outlet 120. The angle formed between line of sight 71 and the direction in which product 11 travels is substantially a right angle. Therefore, non-cracked portions of product 11 normally reflect the signals emitted from bifurcated fiber ending 119 directly back along line of sight 71 to be received by bifurcated fiber ending 119. However, cracked portions of product 11 normally have the opposite result; therefore, the loss of a reflected signal identifies the existence of a crack in product 11.

Figure 10:
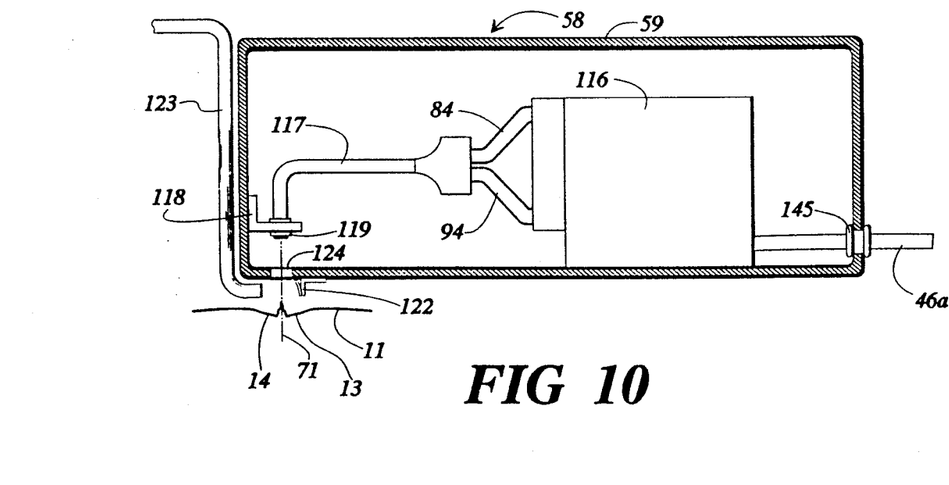
FIG. 10 is a side view of a reflection detector module of a seventh embodiment of the present invention and a portion of a travelling product.

Referring now to FIG. 10, a side view of a reflection detector module 58 of a seventh embodiment of the present invention and a portion of a travelling product 11 are shown. This embodiment of the present invention is very similar in appearance and function to the preceding embodiment shown in FIG. 9. The major difference between the two embodiments is the alternate use of an air supplier. Reflection detector housing 58' is relatively air-tight. Viewing area 124 replaces transceiver air outlet 120 of FIG. 7 to seal reflection detector housing 58'. One example of an acceptable view area 124 is a transparent, plastic lens.

Air is supplied through transceiver air supply 123 which is connected to reflection detector housing 58. Deflector 122 is also connected to reflection detector housing 58. Transceiver air supply 123 is positioned to continuously direct air across transceiver viewing area 124 to prevent obstructions from settling on transceiver viewing area 124. Also, deflector 122 is positioned to further direct air from transceiver air supply 12 downward onto product 11. Air departing from deflector 122 strikes product 11 in much the same way as air from transceiver air outlet 120 of FIG. 9. Non-separated cracks are again separated so that optical signals from bifurcated fiber ending 119 may be used to detect these cracks.

With regard to all embodiments of the present invention, it should be understood that various types of optical signal devices, such as photoelectric, fiber optic, laser devices, and other optical devices, are included within the scope of the present invention. Many of these devices have the ability to automatically adjust the intensity of the light emitted or vary the intensity expected as a product changes consistency.

Whereas the preferred embodiment is disclosed in the form of an edge crack sensor, it is within the scope of the present invention to sense other qualities of a travelling product, utilizing some or all of the inventive concepts disclosed herein. Various other visual variations in a product may also be detected by the present invention. Abrupt changes in the light-reflecting or light-transmitting properties of a product caused by a number of other forces are also detectable. Depending on the type of light employed, the present invention may be used to detect splices in a product by sensing the change in the amount of light which transmitted through a product. Also, the present invention may be used to detect changes in the color of a product defined by an intentional identifying mark or an unintentional defect.

While the embodiments of the present invention which have been disclosed herein are the preferred forms, other embodiments of the method and apparatus of the present invention will suggest themselves to persons skilled in the art in view of this disclosure. Therefore, it will be understood that variations and modifications can be effected within the spirit and scope of the invention and that the scope of the present invention should only be limited by the claims below. Furthermore, the present invention is not limited by those inventive points specifically emphasized as "unique", etc., within this specification.

I claim:

1. Edge crack detector apparatus for detecting cracks on an edge of a travelling product, such as a continuous paper web, and the like, said detector apparatus comprising:
    an air-purged housing, said housing comprising, at least,
        an inner air chamber,
        an air receipt port defining a first opening through said housing into said inner air chamber, and
        an air delivery port defining a second opening through said housing into said inner air chamber, wherein said air delivery port is positioned to direct air at a travelling product to separate edge cracks in the travelling product;
    an optical sensor comprising, at least, a light element connected to said air-purged housing and located, at least partially, within said inner air chamber so that air flowing through said inner air chamber flows across said light element and so that optical signals associated with said light element pass through said air delivery port;
    a linear actuator means connected to said air-purged housing for adjusting positions of said air-purged housing relative to an edge of the travelling product; and
    an edge tracking means connected to said liner actuator means for tracking the edge of the travelling product.

2. Detector apparatus of claim 1, wherein said air-purged housing is so constructed that air flowing through said inner air chamber and across said light element continuously purges space between said light element and said air delivery port.

3. Detector apparatus of claim 1, wherein said air-purged housing further comprises a removable cover, which when removed exposes said inner chamber.

4. Detector apparatus of claim 1, wherein the direction of optical signals associated with said light element forms a right angle with the direction of travel of a monitored travelling product.

5. Detector apparatus of claim 1, wherein the optical sensor further comprises, at least, a transmission medium connected to said light element, and a control element connected to said transmission medium.

6. Detector apparatus of claim 5, wherein the transmission medium and said control element of said optical sensor are enclosed within said inner air chamber.

7. Detector apparatus of claim 5, wherein the transmission medium and said control element of said optical sensor are external to said inner air chamber.

8. Detector apparatus of claim 5, wherein said light element of said optical sensor comprises an optical transceiver means for emitting optical signals through said air delivery port in response to electrical signals received from said control element through said transmission means, and for receiving optical signals through said air delivery port and transmitting electrical signals through said transmission medium in response to receiving the optical signals.

9. Detector apparatus of claim 5, wherein said transmission medium defines an electrical conductor, and wherein said light element defines an optical transducer.

10. Detector apparatus of claim 5, wherein said transmission medium defines a fiber optic cable, and wherein said light element defines a fiber optic cable ending.

11. Edge crack detector apparatus for detecting cracks on an edge of a travelling product, such as a continuous paper web, and the like, said detector apparatus comprising:

an air-purged housing, said air-purged housing comprising, at least,
  an inner air chamber, said inner air chamber being relatively enclosed,
  an air receipt port defining a first opening through said housing into said inner air chamber,
  a first air delivery port defining a second opening through said housing into said inner air chamber, wherein said first air delivery port is positioned to direct air at a first surface of a travelling product, and
  a second air delivery port defining a third opening through said housing into said inner air chamber, wherein said second air delivery port is positioned to direct air at a second opposing surface of the travelling product,
  a passageway through which at least a portion of the travelling product may continuously travel,
  wherein said first air delivery port is displaced from said second air delivery port along a direction parallel to the direction of travel of the travelling product, whereby air flowing through said first air delivery port and air flowing through said second air delivery port exert relatively oppositely directed forces on adjacent portions of a travelling product sufficient to separate non-separated cracks in the portions of travelling product located within the passageway; and
an optical sensor comprising, at least,
  an optical signal emitter connected to said air-purged housing and located, at least partially, within said inner air chamber so that air flowing through said inner air chamber flows across said optical signal emitter and so that light emitted from said optical signal emitter travels through said first air delivery port in a direction having a directional component which is parallel to the travelling direction of the travelling product, and
  an optical signal receiver connected to said air purged housing and located, at least partially, within said inner air chamber so that air flowing through said inner air chamber flows across said optical signal receiver and so that light received by said optical signal receiver travels through said second air delivery port.

12. Detector apparatus of claim 11, wherein said air-purged housing is so constructed that air flowing through said inner air chamber and across said optical signal emitter continuously purges space between said optical signal emitter and said first air delivery port, and wherein said air-purged housing is so constructed that air flowing through said inner air chamber and across said optical signal receiver continuously purges space between said optical signal receiver and said second air delivery port.

13. Detector apparatus of claim 11, wherein said air-purged housing further comprises a removable cover, which when removed exposes said inner chamber.

14. Detector apparatus of claim 11, wherein said optical signal emitter and said optical signal receiver are directed toward one another across the passageway, whereby signals emitted from said optical signal emitter are, if unobstructed while within the passageway, received by said optical signal receiver.

15. Detector apparatus of claim 11, wherein said optical sensor further comprises, at least, a first transmission medium connected to said optical signal emitter, a second transmission medium connected to said optical signal receiver, and a control element connected to said first transmission medium and said second transmission medium.

16. Detector apparatus of claim 15, wherein said control element, said first transmission medium, and said second transmission medium of said optical sensor are enclosed within said inner air chamber.

17. Detector apparatus of claim 16, wherein said control element, at least a portion of said first transmission medium, and at least a portion of said second transmission medium of said optical sensor are located external to said inner air chamber.

18. Detector apparatus of claim 15, wherein said first transmission medium and said second transmission medium define electrical conductors, and wherein said optical signal emitter and said optical signal receiver define optical transducers.

19. Detector apparatus of claim 15, wherein said first transmission medium and said second transmission medium define fiber optic cables, and wherein said optical signal emitter and said optical signal receiver define fiber optic cable endings.

20. Detector apparatus of claim 11, wherein said optical signal emitter defines a laser.

21. Detector apparatus of claim 11, further comprising a linear actuator means connected to said air-purged housing for adjusting positions of said air-purged housing relative to an edge of a travelling product.

22. Detector apparatus of claim 21, further comprising an edge tracking means connected to said linear actuator means for tracking an edge of a travelling product and generating tracking signals for said linear actuator means.

23. Edge crack detector apparatus for detecting cracks on an edge of a travelling product, such as a continuous paper web, and the like, movable along a product path, said detector apparatus comprising:
  a first air means for directing air toward a first surface of a travelling product;
  a second air means for directing air toward a second opposing surface of the travelling product, wherein said second air means is displaced from said first air means along a direction parallel to the direction of travel of the travelling product;
  an optical signal emitter means for directing optical signals toward the first surface of the travelling product; and
  an optical signal receiver means located across a product path from said optical signal emitter means for receiving optical signals emitted from said optical signal emitter means.

24. Detector apparatus of claim 23, wherein said first air means and said optical signal emitter means are arranged so that air which flows from said first air means flows across said optical signal emitter means, and wherein said second air means and said optical signal receiver means are arranged so that air which flows from said second air means flows across said optical signal receiver means.

25. Detector apparatus of claim 23, wherein said optical signal emitter means is so oriented that the angle formed between the direction of optical signals emitted from said optical signal emitter means and the direction of travel of the travelling product is an angle other than a right angle.

26. Detector apparatus of claim 23, wherein said first air means and said second air means define air hoses.

27. Detector apparatus of claim 23, further comprising a linear actuator means connected to said first and second air means, said optical signal emitter means, and said optical signal receiver means for adjusting their positions relative to an edge of a travelling product.

28. Detector apparatus of claim 27, further comprising an edge tracking means connected to said linear actuator means for tracking an edge of a travelling product and generating tracking signals to be used by said linear actuator means to maintain said relative positioning.

29. Method of detecting cracks on an edge of a product travelling in a travelling direction, said method comprising the steps of:
   directing a first stream of air across an emission surface of an optical signal emitter of an optical signal device;
   directing the first stream of air in a first direction toward a first contact area on a first surface of a travelling product;
   directing a second stream of air across a receiving surface of an optical signal receiver of the optical signal device;
   directing the second stream of air in a second direction toward a second contact area on a second surface of the travelling product, wherein the first surface and second surface define opposite sides of the travelling product, and wherein the first contact area and the second contact area are displaced from one another along the travelling direction;
   transmitting optical signals from the optical signal emitter toward the travelling product; and
   receiving the optical signals at the optical signal receiver when a crack in the travelling product passes between the optical signal emitter and the optical signal receiver.

30. Method of claim 29, wherein the optical signals are emitted from the optical signal emitter in a direction having a directional component which is parallel to the travelling direction.

31. Method of claim 29, wherein the first stream of air is directed at a different velocity than the velocity at which the second stream of air is directed.

32. Method of claim 29, further including the step of generating crack signals upon receiving transmitted optical signals at the optical signal receiver.

33. Method of claim 29, further including the steps of tracking the edge of the travelling product,
   generating edge-sensing signals which indicate proximity to the edge of the travelling product, and
   moving the optical signal emitter and transmitter in response to the edge-sensing signals.

34. Method of detecting cracks on an edge of a product travelling in a travelling direction, said method comprising the steps of:
   locating a sensing unit at an edge of a travelling product, wherein the sensing unit includes a housing with a viewing aperture and an optical transceiver located inside the housing and over the viewing aperture;
   directing a stream of air across the optical transceiver to maintain cleanliness of the transceiver by purging all space between the optical transceiver and the viewing aperture;
   further directing the stream of air toward a travelling product to separate edge cracks;
   transmitting optical signals from the optical transceiver toward the travelling product to sense edge cracks; and
   tracking the edge of the travelling product by generating edge-sensing signals which indicate proximity to the edge of the travelling product, and moving the optical transceiver in response to the edge-sensing signals.

35. Method of claim 34, further including the steps of generating crack signals upon sensing edge cracks and transmitting the crack signal to a control device.

* * * * *